(12) United States Patent
Pearce et al.

(10) Patent No.: US 8,011,132 B2
(45) Date of Patent: Sep. 6, 2011

(54) ENHANCED SHELF LIFE AND ON SEED STABILIZATION OF LIQUID BACTERIUM INOCULANTS

(75) Inventors: Jeremy David Pearce, Bosham (GB); Mary Ann Carpenter, Littlehampton (GB)

(73) Assignee: Becker Underwood Inc., Ames, IA (US)

( * ) Notice: Subject to any disclaimer, the term of this patent is extended or adjusted under 35 U.S.C. 154(b) by 306 days.

(21) Appl. No.: 11/020,714

(22) Filed: Dec. 23, 2004

(65) Prior Publication Data
US 2006/0150488 A1    Jul. 13, 2006

(51) Int. Cl.
*A01C 1/06* (2006.01)
*A01C 21/00* (2006.01)

(52) U.S. Cl. ............... 47/57.6; 47/58.1 SE; 504/100

(58) Field of Classification Search ............ 47/57.6, 47/58.1 SE; 504/100
See application file for complete search history.

(56) References Cited

U.S. PATENT DOCUMENTS

| | | | |
|---|---|---|---|
| 4,337,077 A | | 6/1982 | Rutherford .............. 71/9 |
| 4,849,005 A | * | 7/1989 | Williams et al. ........ 71/7 |
| 4,875,921 A | * | 10/1989 | Paau ...................... 71/7 |
| 5,113,619 A | * | 5/1992 | Leps et al. ............. 47/57.6 |
| 5,137,747 A | * | 8/1992 | Malandain et al. ..... 427/4 |
| 5,292,507 A | | 3/1994 | Charley ................. 424/93 K |
| 5,695,541 A | * | 12/1997 | Kosanke et al. ........ 71/7 |
| 5,697,186 A | | 12/1997 | Neyra et al. ............ 47/57.6 |
| 5,916,029 A | | 6/1999 | Smith et al. ............ 47/57.6 |
| 6,606,822 B2 | * | 8/2003 | Bonfiglio ............... 47/57.6 |
| 6,610,531 B1 | * | 8/2003 | Mateczun et al. ...... 435/260 |
| 6,698,137 B2 | | 3/2004 | Muhr .................... 47/57.6 |
| 7,022,649 B2 | * | 4/2006 | Magri .................... 504/117 |
| 2002/0050096 A1 | * | 5/2002 | Bonfiglio ............... 47/57.6 |
| 2002/0058327 A1 | | 5/2002 | Loh et al. ............... 435/252.2 |
| 2002/0104262 A1 | | 8/2002 | Muhr .................... 47/57.6 |
| 2003/0060496 A1 | | 3/2003 | Merritt et al. .......... 514/383 |
| 2003/0228679 A1 | | 12/2003 | Smith et al. ............ 435/235.1 |
| 2004/0081714 A1 | | 4/2004 | Pauly et al. ............ 424/774 |
| 2004/0092400 A1 | * | 5/2004 | Magri .................... 504/117 |
| 2004/0102328 A1 | | 5/2004 | Johnson et al. ........ 504/350 |
| 2007/0074451 A1 | * | 4/2007 | Pearce et al. .......... 47/57.6 |

FOREIGN PATENT DOCUMENTS

| | | |
|---|---|---|
| EP | 0 203 708 | 6/1991 |
| EP | 0 410 862 B1 | 7/1995 |
| RU | 2052507 C1 | 1/1996 |
| SU | 1673973 A1 | 8/1991 |

OTHER PUBLICATIONS

Mugnier et al. 1985. Survival of bacteria and fungi in relation to water activity and the solvent properties of water in biopolymer gels. Applied and Environmental Microbiology 50(1): 108-114.*
Streeter, J.G.; "Effect of trehalose on survival of Bradyrhizobium japonicum during desiccation," Journal of Applied Microbiology, 2003, 95, pp. 484-491. (8 pages total).*
Roughley, R. J. "The Preparation and Use of Legume Seed Inoculants," Plant and Soil, 32, 675-701 (1970).*
Singleton et al. "Development and Evaluation of Liquid Inoculants," ACIAR Proceedings 109e, printed version 2002, pp. 52-66.*
Juan Carlos Argüelles, "Physiological Roles of Trehalose in Bacteria and Yeast: a Comparative Analysis," Arch Microbiol (2000) 174:217-224.
Crowe, et al., "Preservation of Membranes in Anhydrobiotic Organisms: The Role of Trehalose," Science, New Series, vol. 223. No. 4637, (Feb. 17, 1984), 701-703.
B. Boboye, "Degradation of Trehalose by Rhizobia and Characteristics of a Trehalose-Degrading Enzyme Isolated from Rhizobium Species NGR234," Journal of Applied Microbiology (2004), 97: 256-261.
Maurice, et al., "Survival and Change in Physiological State of Bradyrhizobium Japonicum in Soybean (Glycine max L. Merril) Liquid Inoculants After Long-Term Storage," World Journal of Microbiology & Biotechnology (2001), 17: 635-643.
Mary, et al., "Production and Survival During Storage of Spray-Dried Bradyrhizobium Japonicum Cell Concentrates," Journal of Applied Bacteriology (1993), 74: 340-344.
Obaton, et al., "Are Bradyrhizobium Japonicum Stable During a Long Stay in Soil?" Plant and Soil (2002), 245: 315-326.
Cliquet, et al., "Influence of Culture Medium and Growth Stage on the Survival of Bradyrhizabium Japonicum During Desiccation and Storage at Two Relative Humidities," Symbiosis (1994), 16: 279-287.
Mary, et al., "Differences Among Rhizobium Meliloti and Bradyrhizobium Japonicum Strains in Tolerance to Desiccation and Storage at Different Relative Humidities," Soil Biol. Biochem. vol. 26, No. 9 (1994), 1125-1132.
Ping Xie, et al., "Accumulation of Soluble Carbohydrates, Trehalase and Sucrose Synthase in Effective (Fix+) and Ineffective (Fix−) Nodules of Soybean Cultivars that Differentially Nodulate with Bradyrhizobium Japonicum," Functional Plant Biology (2003), 30: 965-971.
Mashhady, et al., "Effect of Salinity on Survival and Symbiotic Performance Between Rhizobium Meliloti and Medicago Saliva L. in Saudi Arabian Soils," Arid Soil Research and Rehabilitation (1998), 12: 3-14.
Ghittoni, et al., "Peanut Rhizobia Under Salt Stress: Role of Trehalose Accumulation in Strain ATCC 51466," Can. J. Microbiol (1995), 41: 1021-1030.
Sussich, et al., "Reversible Dehydration of Trehalose and Anhydrobiosis: From Solution State to an Exotic Crystal?," Carbohydrate Research (2001), 334: 165-176.

(Continued)

*Primary Examiner* — Susan McCormick Ewoldt
(74) *Attorney, Agent, or Firm* — Drinker Biddle & Reath LLP

(57) ABSTRACT

The present invention includes a method for producing a liquid inoculant containing a desiccant. The method can improve survival and stability of bacteria in liquid inoculants in pack and on seeds. The method includes providing a liquid inoculant of a bacteria grown to a substantially stationary phase. A desiccant treatment containing a desiccant is added to the liquid inoculant to form a partially desiccated inoculant product. The partially desiccated inoculant product can be packaged and stored. The partially desiccated inoculant product can also be applied to seeds.

25 Claims, 8 Drawing Sheets

OTHER PUBLICATIONS

Thorne, et al., "Cell Density-Dependent Starvation Survival of Rhizobium Leguminosarum bv. Phaseoli: Identification of the Role of an N-Acyl Homoserine Lactone in Adaptation to Stationary-Phase Survival," Journal of Bacteriology, Feb. 1999, 981-990.

Zayed, et al., "Influence of Trehalose and Moisture Content on Survival of Lactobacillus Salivarius Subjected to Freeze-Drying and Storage," Process Biochemistry (2004), 39: 1081-1086.

Leslie, et al., "Trehalose and Sucrose Protect Both Membranes and Proteins in Intact Bacteria During Drying," Applied and Environmental Microbiology, Oct. 1995, 3592-3597.

Athar, et al., "Effect of Drought on the Growth and Survival of Rhizobium Meliloti Strains from Pakistan and Nepal," Journal of Arid Environments (1997), 35:335-340.

Müller, et al., "Trehalose Affects Sucrose Synthase and Invertase Activities in Soybean (Glycine Max [L.] Merr.) Roots," Journal of Plant Physiology (1998), 153: 255-257.

Maruta, et al. "Cloning and Sequencing of Trehalose Biosynthesis Genes from Rhizobium sp. M-11," Biosci. Biotech. Biochem. (1996), 60(4): 717-720.

Thorne, et al., "Adaptation to Nutrient Starvation in Rhizobium Leguminosarum bv. Phaseoli: Analysis of Survival, Stress Resistance, and Changes in Macromolecular Syntheses During Entry to and Exit from Stationary Phase," Journal of Bacteriology, Nov. 1997, 6894-6901.

Souzu, "Basic Aspects and Industrial Strategies for the Preservation of Microorganism by Freezing and Drying".

Temprano, et al., "Survival of Several Rhizobium/Bradyrhizobium Strains on Different Inoculant Formulations and Inoculated Seeds," Int. Microbiol (2002), 5: 81-86.

Large Soviet Encyclopedia, 1972, vol. 8, p. 133, (in Russian—no translation).

Dandekar et al. "*Agrobacterium-Mediated Transformation of Somatic Embryos as a Method for the Production of Transgenic Plants*," Journal of Tissue Culture Methods, vol. 12. No. 4, pp. 145-150, 1989.

Singleton et al. "*Development and Evaluation of Liquid Inoculants*," ACIAR Proceedings 109e, printed version published 2002, pp. 52-66.

\* cited by examiner

US 8,011,132 B2

ENHANCED SHELF LIFE AND ON SEED STABILIZATION OF LIQUID BACTERIUM INOCULANTS

TECHNICAL FIELD

The invention relates to liquid inoculants. Particularly, the invention relates to a method for improving survival and stability of bacteria of liquid inoculants in pack and when applied to seeds.

BACKGROUND OF THE INVENTION

Various microorganisms are known to have a beneficial effect on plants. These microorganisms include bacteria of the genera Rhizobium, Bradyrhizobium, Pseudomonas, Serratia, Bacillus, Paenibacillus, Pasteuria, Azotobacter, Enterobacter, Azospirillum, Methylobacterium, Cyanobacteria, and mycorrhizal fungae. Such microorganisms can be introduced to the plants by the use of inoculant compositions. The process by which inoculant compositions are created includes the step of fermenting the microorganisms, generally on a nutrient media.

The inoculant compositions can be applied directly onto seeds of plants or can be applied in furrow immediately prior to the seeds being planted. Inoculation of the seeds or soil with beneficial microorganisms for crop improvement has been practiced for a number of years. However, variable and inconsistent results have often been observed, possibly due to loss of inoculant viability or variability of dosage due to changes in inoculant viability.

When an inoculant is applied at the time of sowing, whether in furrow application or by on-seed application, the microorganisms in the inoculant do not have time to adjust to the new environment. Consequently, the microorganisms in the inoculant may have a low rate of survival.

Currently, to improve viability of the microorganisms in the inoculant, extenders based on sugars or polymers are added when the inoculant is added to the seed, or at the time of sowing. Because the extenders are added after packaging of the inoculant, the extenders have no effect on the survival and stability of the inoculant in pack.

Also, the addition of extenders at the time the inoculant is added to the seed or at the time of sowing is cumbersome and generally must be performed by the end-users of the inoculant (e.g., farmers) in a non-controlled environment (e.g., in a barn or in a farm field). Thus, there is an increased likelihood that the extenders will be improperly applied.

To overcome the problems associated with adding extenders after the inoculant is prepared, extenders have also been added to the nutrient medium prior to the fermentation step of creating the liquid inoculant. However, addition of the extenders, at an optimal level for on-seed survival, before fermentation inhibits growth of the microorganisms.

Therefore, there is a need for a method for increasing survival and stability of a microorganism (e.g., bacteria) of a liquid inoculant during storage, and for improving on-seed survival and stability of a microorganism of a liquid inoculant once placed on a seed.

SUMMARY OF THE INVENTION

One embodiment of the present invention is a method for preparing a liquid inoculant product containing a desiccant. The method includes providing a liquid inoculant of a bacteria grown to a substantially stationary phase. A desiccant treatment comprising a desiccant is added to the liquid inoculant to form a partially desiccated inoculant product.

In another embodiment of the present invention, the partially desiccated inoculant product is packaged and stored.

In a further embodiment of the present invention, the partially desiccated inoculant is applied to a seed.

DETAILED DESCRIPTION OF THE DRAWINGS

Figure 1:
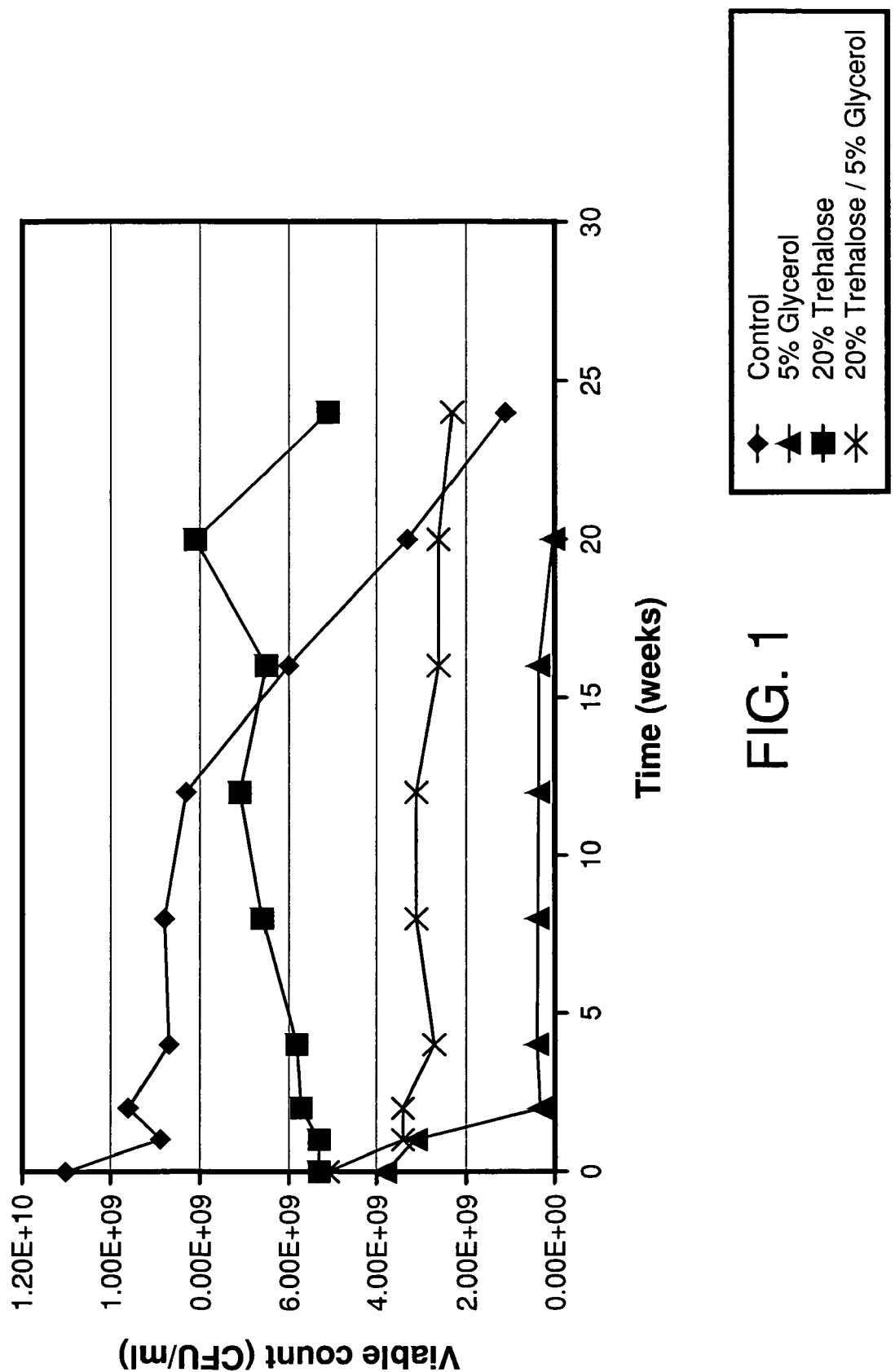
FIG. 1 is a graph of Bradyrhizobium japonicum ("B japonicum") survival in a liquid broth, as a function of time and temperature, resulting from the practice of several embodiments of the present invention.

A method for preparing a liquid inoculant of a bacteria is provided. The method includes the addition of a desiccant to the liquid inoculant after the bacteria have been grown to a substantially stationary phase. The addition of the desiccant to the inoculant forms a partially desiccated inoculant product.

The method can provide for increased stability of the bacteria when the partially desiccated inoculant product is "in pack" (i.e., contained in a package) and when the partially desiccated inoculant product is applied onto a seed. The increased stability can result in enhanced survival of the bacteria both in pack and on seed.

Bacteria are introduced to a liquid nutrient media to create a bacterial culture. Various bacteria, including but not limited to bacteria of the genera Rhizobium, Bradyrhizobium, Pseudomonas, Serratia, Bacillus, Paenibacillus, Pasteuria, Azotobacter, Enterobacter, Azospirillum, Methylobacterium, Cyanobacteria (blue-green algae), can be introduced to the liquid nutrient media. Other microorganisms (e.g., mycorrhizal fungae) can be introduced to the liquid nutrient media to create the bacterial culture. For Rhizobium and Bradyrhizobium, preferred strains include Bradyrhizobium japonicum, Rhizobium meliloti, Rhizobium leguminosarum biovar trifolii, Rhizobium leguminosarum biovar viceae and Rhizobium leguminosarum biovar phaseoli. These bacteria are capable of forming nodules in the roots of species of leguminous plants. Although the following description is mainly directed to *Rhizobium* inoculant compositions, it will be appreciated that similar principles apply to the use of other microorganisms.

The liquid nutrient media into which the bacteria are introduced can be any liquid nutrient media known to those skilled in the art to be compatible with the bacteria chosen. For example, YMB is a commonly used medium for *Rhizobium*. The composition of YMB is presented in Table 1.

TABLE 1

Characteristics of YMB

| Yeast Extract | 0.50 g/L |
|---|---|
| Mannitol | 10.0 g/L |
| K2HPO4 | 0.50 g/L |
| MgSO4•7H2O | 0.2 g/L |
| NaCl | 0.1 g/L |
| Water | 1 L |
| pH | 6.8 |

After the bacteria is added to the liquid nutrient media, the bacterial culture can then be incubated (or fermented) to allow the bacteria to grow to a "substantially stationary phase". The "substantially stationary phase" is defined to include the culture period from late "log phase" to "stationary phase". The "log phase" is defined as the phase that occurs after the lag phase at the beginning of fermentation and as the phase where nutrients are generally unlimited and where there is generally exponential growth of the bacteria. The "stationary phase" is defined as the phase that occurs after the log phase and as the phase in which bacterial growth has essentially ceased. The stationary phase is generally reached when the liquid nutrient media is substantially exhausted. As used herein, the substance containing the bacteria that is incubated to the substantially stationary phase is termed a "liquid inoculant".

Generally, the bacteria incubation period can be between 1 and 15 days. More specifically, the incubation period can be between 2 and 7 days. During the incubation period the liquid nutrient media and bacteria can be aerated and maintained at a temperature suitable for growth. Aeration can be performed through the use of a shaking incubator, a fermentation reactor, or other similar means. The precise conditions for incubation depend on the type of bacteria and the type of liquid nutrient media used. For example, *B japonicum* can be incubated on a nutrient media in a shaking incubator for about 1-10 days at temperatures from about 20° C. to about 35° C. Preferably, *B japonicum* is incubated for about 2-7 days at about 28° C. to allow the bacteria to grow.

The bacteria count at the substantially stationary phase varies depending on the bacteria. For example, for *Rhizobium* bacteria, bacteria counts in the liquid inoculant from about $1 \times 10^9$/ml to about $1 \times 10^{11}$/ml are contemplated. More particularly, the liquid inoculant comprises about $1 \times 10^{10}$/ml. These are exemplary amounts, and as such other amounts are contemplated to be within the scope of the present invention.

After the substantially stationary phase is attained (i.e., after the bacteria has been allowed to grow at an exponential rate rate), a desiccant treatment containing a desiccant is introduced into the liquid inoculant to create a partially desiccated inoculant product. The term "desiccant treatment" means a mixture of a desiccant and a diluting substance, generally water. The term "desiccant" means a substance that, when added to water, reduces water activity (which is defined as the partial pressure of water vapour at the surface of the substance divided by saturation pressure). Reduction of water activity to a level less than 0.995 is contemplated to be effective in enhancing in pack survival of the bacteria in the partially desiccated inoculant product. Reduction of water activity to a level less than 0.990, preferably less than about 0.980, is contemplated to be effective in enhancing on seed survival of the bacteria in the partially desiccated inoculant product.

As used herein, "desiccants" can include any compound or mixture of compounds that can be classified as a desiccant regardless of whether the compound or compounds are used in such concentrations that they in fact have a desiccating effect on the liquid inoculant. Examples of suitable desiccants include one or more of trehalose, sucrose, glycerol, and triethylene glycol. Other suitable desiccants include, but are not limited to, non reducing sugars and sugar alcohols (e.g., mannitol).

The amount of desiccant introduced into the liquid inoculant generally is in a concentration from about 5% to about 50% by weight/volume of the partially desiccated inoculant product. When the desiccant is trehalose, the desiccant is preferably in a concentration from about 10% to about 40% by weight/volume of the partially desiccated inoculant product. More preferably, the trehalose is in a concentration from about 20% to about 30% by weight/volume of the partially desiccated inoculant product.

The desiccant treatment can include a mixture of more than one desiccant. In fact, the mixtures can be any combination of two or more desiccants, as desiccant is defined herein. For example, the desiccant treatment can include a mixture of trehalose and glycerol, a mixture of trehalose and sucrose, or a mixture of sucrose and triethylene glycol. A mixture of trehalose and glycerol can include trehalose in concentrations from about 5% to about 40% by weight/volume of the partially desiccated inoculant product and glycerol in concentrations from about 1% to about 10% by weight/volume of the partially desiccated inoculant product. More particularly, the concentrations of the trehalose and the glycerol in the mixture can be about 20% and about 5% by weight/volume of the partially desiccated inoculant product, respectively.

The desiccant can be added to the liquid inoculant while the liquid inoculant is still in the vessel used during incubation (e.g., fermentation reactor or shaking incubator). Alternatively, the desiccant can be added to the liquid inoculant during packaging.

In one embodiment, sufficient desiccant is present to at least partially desiccate the bacteria in the partially desiccated inoculant product, thereby: (1) improving the stability and survival of the bacteria in subsequent steps such as packaging and storing, (2) and improving the stability and survival of the bacteria in subsequent steps such as on-seed application of the partially desiccated inoculant product.

The partially desiccated inoculant product can then be packaged and stored. The packaging can be any standard packaging known in the industry. For example, the partially desiccated inoculant product can be packaged in polyethylene bladders.

After packaging the partially desiccated inoculant product can be stored. The storage conditions can include refrigerated to ambient temperatures and low to moderate relative humidity. Preferably, storage conditions include a temperature below about 35° C. and a relative humidity below about 80%.

The partially desiccated inoculant product can be applied to a variety of seeds. For example, the partially desiccated inoculant product can be applied to seeds for leguminous plants. Leguminous plants form a large group of plants including vegetables of economic importance such as soybean, lucerne (alfalfa), peanut, peas, beans, and the like. The bacteria of the partially desiccated inoculant product can colonize the rhizosphere and/or infect the roots of the plants, as they permeate into the radicular hairs and colonize the root, producing nodules. As a result of this symbiotic relation, plants can turn gaseous nitrogen into organic compounds of nitrogen through nitrogen fixation. The plants then can use these organic compounds to grow.

The number of bacteria on a seed at the time the partially desiccated inoculant product is applied to the seed varies. The number of bacteria on the seed 10 weeks after the partially desiccated inoculant product is applied can also vary, but it is contemplated that the number should not represent a significant departure from the original amount. In other words, there should not be a sharp decline in bacteria count/seed over time. For example, if the number of bacteria on a seed is at least $6 \times 10^5$ at the time the partially desiccated inoculant product is applied to the seed, the number of bacteria on the seed after about 10 weeks is preferably at least $1 \times 10^5$.

To improve stability and survival of the bacteria in the partially desiccated inoculant product in pack and on seeds, it is contemplated that a polymer can be optionally added to the partially desiccated inoculant product prior to applying the partially desiccated inoculant product to the seed. The polymer can be added before the packaging step or after the storing step. The polymer can include polyvinyl pyrrolidone, alkylated vinyl pyrrolidone polymers, vinyl pyrrolidone and vinyl acetate copolymers, vinyl pyrrolidone and styrene copolymers, polyvinyl alcohol polymers, and other similar polymers. The polymer can be in a concentration from about 1% and 25% weight/volume of the partially desiccated inoculant product.

Although the addition of the desiccant to the liquid inoculant to create a partially desiccated inoculant product after the bacteria has reached the substantially stationary phase improves stability of bacteria without the necessity of adding an extender at the time of sowing, it does not preclude the use of an extender. In fact, it is within the scope of the present invention that extenders can be applied to seeds after the partially desiccated inoculant product has been applied to the seed. The extender can be added at the time of sowing or at the time of seed application of the partially desiccated inoculant product. The extenders can include any commonly used extenders such as those based on sugars, gums, carboxymethyl cellulose, and polymers.

The partially desiccated inoculant product can be applied to peat, clay and/or other similar dry carriers to form a dry, flowable inoculant formulation. The partially desiccated inoculant product can be applied by spraying or other known means.

The invention will now be illustrated with the following non-limiting examples.

EXAMPLE 1

Evaluation of Stability of *Bradyrhizobium japonicum* in the Presence of Trehalose and a Glycerol/Trehalose Mixture

*B japonicum* was cultured in shake flasks on a nutrient media for 7 days at 28° C. in a shaking incubator to create a 7 day old mature fermentation broth. Four treatments (see Table 2) were prepared in 250 ml shake flasks. The treatments were prepared in duplicate, so there was a total of 8 250 ml shake flasks. 50 ml of the seven day old mature fermentation broth was added to each of the shake flasks. The contents of all the flasks were allowed to equilibrate in a shaking incubator for an additional 7 days at 28° C. After equilibrium was attained, one flask from each of the treatments was transferred to static incubation at 28° C. The second flask from each of the treatments was transferred to static incubation at 35° C.

TABLE 2

Treatments - Influence of trehalose and glycerol on stability of *B japonicum*

| Treatments | Water(g) | Glycerol(g) | Trehalose(g) | Symbol on FIGS. |
|---|---|---|---|---|
| Control 0% trehalose 0% glycerol | 50 | 0 | 0 | ◆ |
| 20% trehalose | 30 | 0 | 20 | ■ |
| 5% glycerol | 45 | 5 | 0 | ▲ |
| 5% glycerol + 20% trehalose | 25 | 5 | 20 | ✳ |

Samples were periodically taken from the flasks and total viable plate counts were conducted to assess the number of surviving bacteria. Plate counts were performed by first mixing the sample and then, using a calibrated pipette and sterile tip, removing 1 ml of the sample and placing it into a test tube with 9 ml of reverse osmosis (RO) water, thereby creating a $10^{-1}$ dilution. Then using a 1000 µL Rainin (calibrated and set to 1000 µL) and sterile tips, 1000 µL of the $10^{-1}$ dilution was removed from the $10^{-1}$ dilution test tube and transferred into another test tube containing 9 ml RO water, thereby creating a $10^{-2}$ dilution. These steps were then repeated up to a $10^{-7}$ dilution, noting that the test tubes containing the dilutions were vortexed and flamed between each transfer.

Using a 100 µL Rainin (calibrated and set to 30 µL) and sterile tips, 30 µL from the $10^{-1}$ dilution test tube was removed and three 10 µL drops were placed onto a nutrient agar plate, which served as a contamination detection plate. The nutrient agar was Oxoid. These steps were repeated for the other dilutions, except that for the $10^{-5}$, $10^{-6}$, and $10^{-7}$ dilutions, the samples were placed on standard plates of Congo Red Yeast Mannitol Agar ("CRYMA"—See Table 3).

TABLE 3

Composition of CRYMA Plates

| Ingredient | Amount |
|---|---|
| $MgSO_4$ | 0.204 g |
| NaCl | 0.1 g |
| $K_2HPO_4$ | 0.5 g |
| Yeast Extract (Difco) | 0.4 g |
| Mannitol | 10.0 g |
| Congo Red (0.25% solution) | 10 ml |
| Agar (BBL) | 15 g |

The plates were allowed to dry before inverting them and placing them into an incubator at 28° C. for 5 days. After 5 days, the number of colonies were counted under a low power microscope. The total count was calculated by taking the mean×dilution×100.

Figure 2:
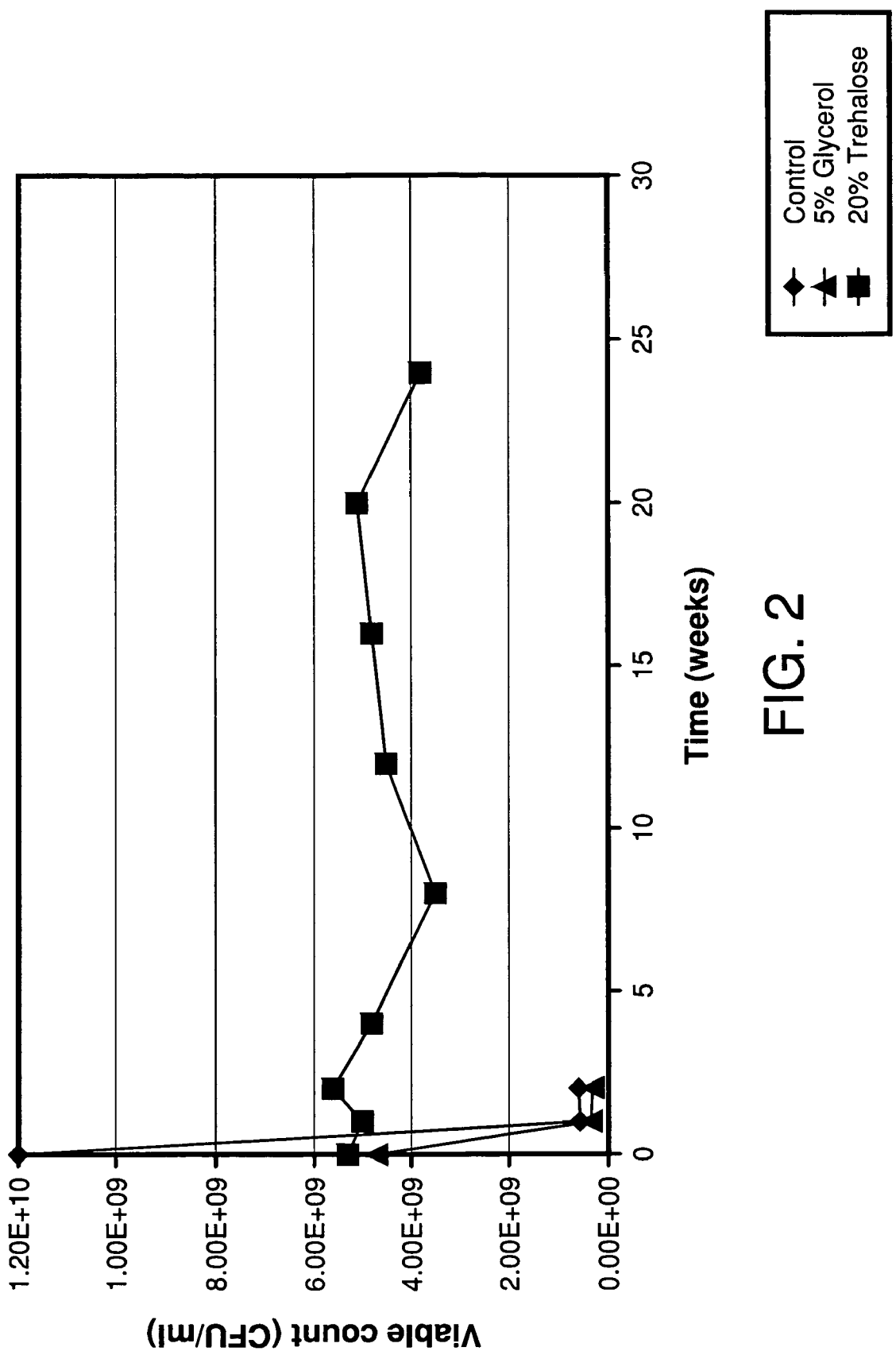
FIG. 2 is a graph of B japonicum survival in a liquid broth, as a function of time and temperature, resulting from the practice of several embodiments of the present invention.

The results of the four treatments with regard to the survival of *B japonicum* incubated in a liquid broth at 28° C. are shown in FIG. 1. The results of the treatments with regard to the survival of *B japonicum* incubated in a liquid broth at 35° C. are shown in FIG. 2. The treatment with 5% glycerol became contaminated during testing and thus is not included in FIG. 2.

The results shown in FIG. 1 indicate that at 28° C., the 20% trehalose treatment and the 20% trehalose/5% glycerol treatment provide for good survivability of the bacteria in the liquid broth. The bacteria count in the control began to decrease some time between about 12 weeks and 16 weeks from the initiation of the experiment. In contrast, the bacteria count in the 20% trehalose treatment and the 20% trehalose/5% glycerol treatment remained at a relatively constant level during that same time period and even after that time period.

The results shown in FIG. 2 indicate that at 35° C., the 20% trehalose treatment provided for good survivability of the bacteria in the liquid broth. While the bacteria count of the other treatments, including the control treatment, decreased dramatically early in the experiment, the bacteria count of the 20% trehalose treatment remained relatively constant throughout the experiment.

After 10 weeks, samples were taken from the control and 20% trehalose treatment and applied to soya seeds. The seeds were incubated at 22° C. Periodically samples were taken and the number of surviving *B japonicum* was assessed. The method of assessing on-seed survival was as follows.

Soya seed lots of 500 g were weighed and placed into clean labelled resealable plastic bags. Using a 2 ml syringe or sterile 2 ml pipette, 1.38 ml of a treatment was evenly dispensed onto the seed surfaces. Ambient air was then trapped in the now seed inoculated plastic bag. The plastic bag was then immediately sealed and shaken until the seeds were evenly covered with the treatment (approximately 30 seconds). The plastic bag was unsealed and placed out of direct sunlight in ambient laboratory conditions (21° C.) until dry (approx 10 minutes). Using a dry alcohol-wiped full length scoop-spatula, exactly 100 intact seeds were randomly selected from the plastic bag. The seeds were placed into a pre-prepared 100 ml dilution bottle. The bottle was closed and then immediately shaken vigorously for approximately 1 minute. Using aseptic technique, from the prepared 100 ml bottle, serial dilutions of the suspension were prepared as follows: (1) immediately after shaking the 100 ml bottle, 1 ml of suspended bacteria and diluent was aseptically transferred into a first 9 ml dilution tube of RO water, thereby creating a $10^{-1}$ dilution (2) the $10^{-1}$ dilution was vortexed for 15 seconds, (3) immediately after vortexing, 1 ml of the $10^{-1}$ dilution was transferred into another 9 ml dilution tube of RO water to create a $10^{-2}$ dilution (4) the $10^{-2}$ dilution was then vortexed; (5) steps (3) and (4) were repeated to achieve $10^{-3}$ and $10^{-4}$ dilutions.

Colony assessment agar plates were then labelled with the details of the dilution tube used, treatment details, and plating date. Duplicate plates were created for each dilution. Prior to taking a sample from the dilution tubes and placing them on the agar plates, the dilutions were vortexed. Then, using standard aseptic pipetting techniques, 100 μL samples of each of the dilutions were dispensed centrally onto each agar plate. Using a sterile spreader, the samples were spread evenly over the surfaces of the plates. The plates were then incubated for 7 days at 28° C. After incubation, the number of colony forming units (CFU) on each plate were counted and recorded. Then, the following calculation was used to determine the number of CFU/plate: [Mean colonies×{labelled dilution×$10^{(a)}$×$100^{(b)}$}/$100^{(c)}$], where (a) is the correction value for 0.1 ml/plate from dilution, (b) is the correction value for 100 ml in original dilution bottle, and (c) is the correction value for number of seeds in original sample.

Figure 3:
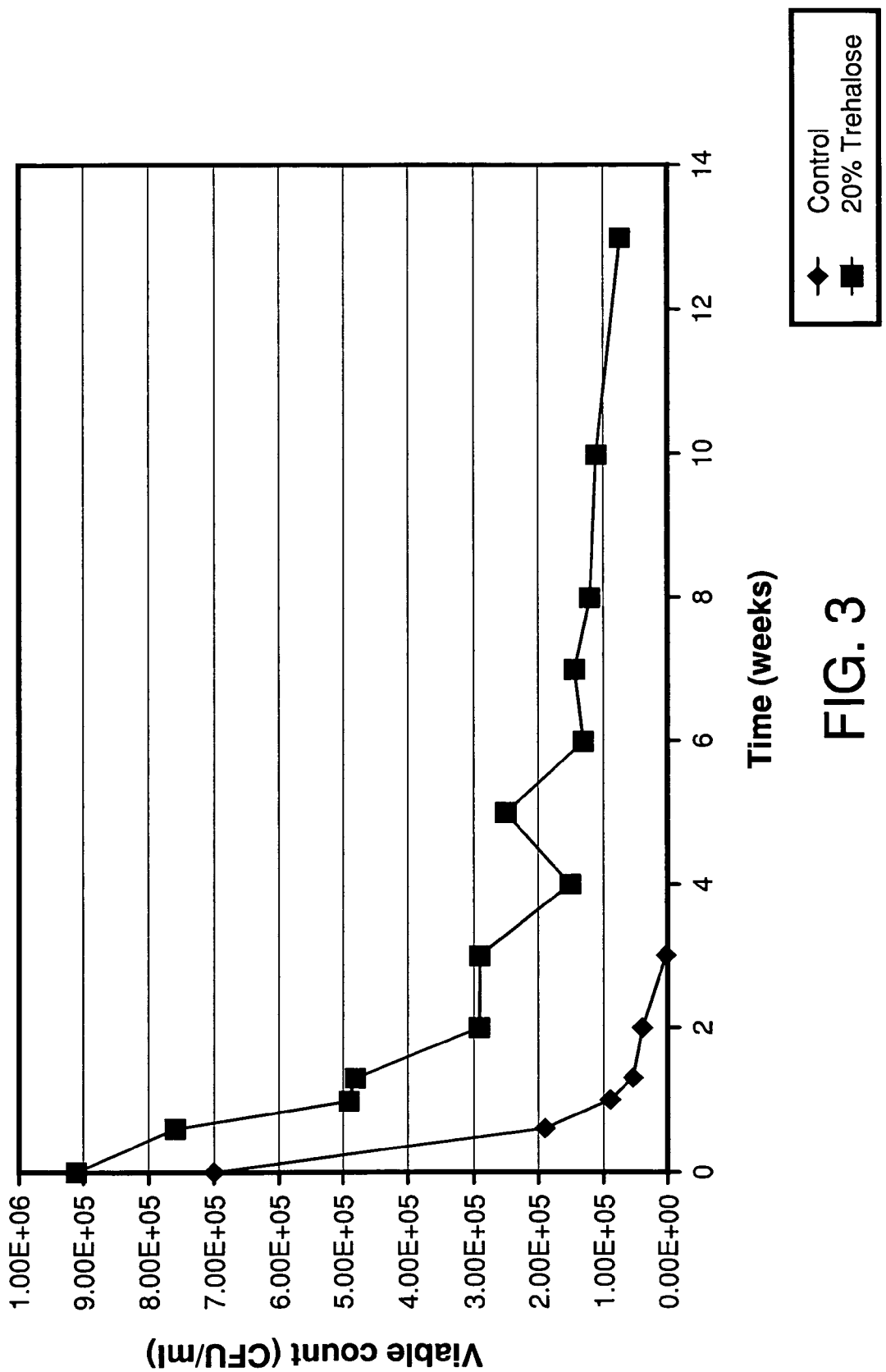
FIG. 3 is a graph of B japonicum survival on seed, as a function of time and temperature, resulting from the practice of several embodiments of the present invention.

The results of the on seed survival of *B japonicum* after 10 weeks are shown in FIG. 3. The results show that the length of time the bacteria count exceeded 1×$10^5$/seed was less than 1 week for the control treatment, but greater than 10 weeks for the 20% trehalose treatment. These results indicate that the treatment with trehalose concentrations at 20% provides for good survivability of the bacteria when the bacteria are placed on seeds.

EXAMPLE 2

Optimization of the Level of Trehalose/Sucrose Required to Stabilize *B japonicum*

The procedure followed for the preparation of the flasks was the same as in Example 1. The treatments for this example are given in Table 4.

TABLE 4

Treatments - Influence of trehalose and sucrose on stability of *B japonicum*

| Treatment | Water(g) | Trehalose(g) | Sucrose(g) |
|---|---|---|---|
| Control | 50 | 0 | 0 |
| 5% trehalose | 45 | 5 | 0 |
| 10% trehalose | 40 | 10 | 0 |
| 20% trehalose | 30 | 20 | 0 |
| 30% trehalose | 20 | 30 | 0 |
| 40% trehalose | 10 | 40 | 0 |
| 5% sucrose | 45 | 0 | 5 |
| 10% sucrose | 40 | 0 | 10 |
| 20% sucrose | 30 | 0 | 20 |
| 30% sucrose | 20 | 0 | 30 |

Figure 4:
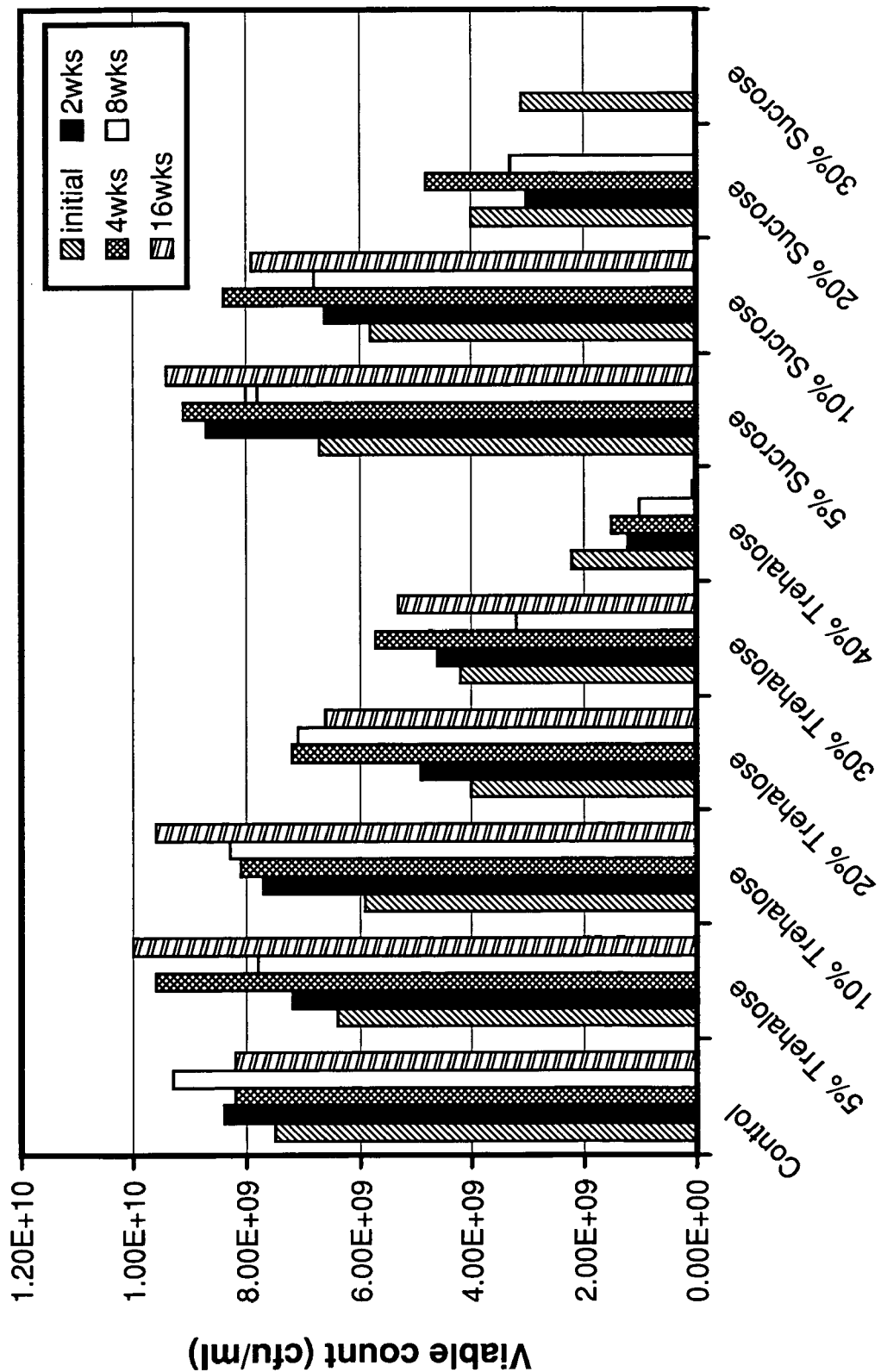
FIG. 4 is a graph of B japonicum survival in a liquid broth, as a function of the type and amount of desiccant, resulting from the practice of several embodiments of the present invention.

The results of the treatments with regard to the survival of *B japonicum* incubated in a liquid broth at 28° C. are shown in FIG. 4. The results of the treatments with regard to the survival of *B japonicum* incubated in a liquid broth at 35° C. are shown in FIG. 5.

The results shown in FIG. 4 indicate that at 28° C., treatments with trehalose concentrations between 10% and 30% weight/volume are optimal for survival of the bacteria in the liquid broth. FIG. 4 also indicates that treatments with sucrose concentrations between 5% and 10% weight/volume are favorable to the survival of the bacteria in the liquid broth, but not to the same extent as the trehalose treatments. FIG. 4 also indicates bacteria can survive treatments with trehalose concentrations at 40%, showing that the bacteria has to the potential to survive in a formulation that is inhibitory to growth of microorganisms.

Figure 5:
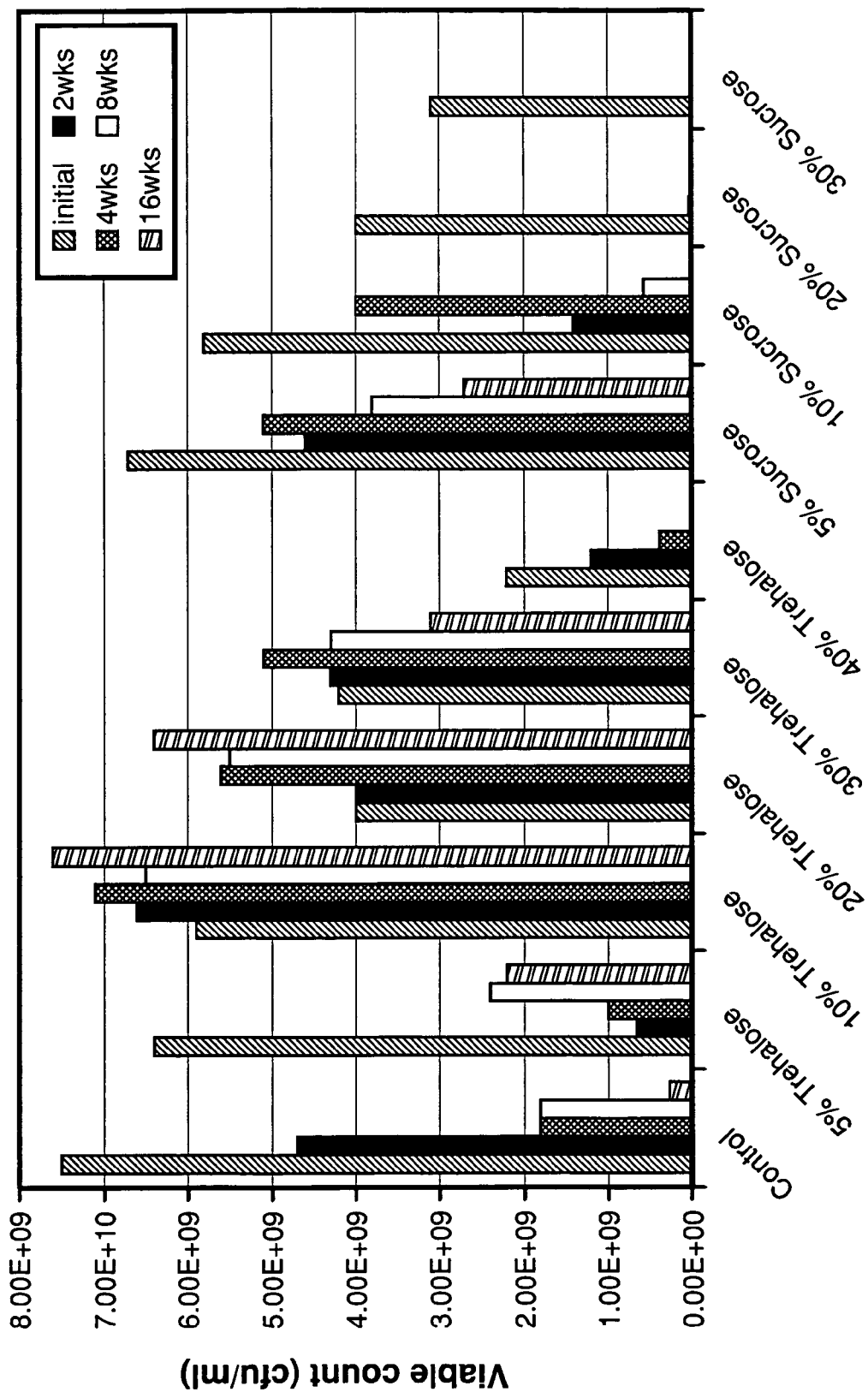
FIG. 5 is a graph of B japonicum survival in a liquid broth, as a function of the type and amount of desiccant, resulting from the practice of several embodiments of the present invention.

The results shown in FIG. 5 indicate that at 35° C., treatments with trehalose concentrations between 10% and 30% weight/volume are optimal for survival of the bacteria in the liquid broth. FIG. 5 also indicates that treatments with sucrose concentrations at 5% weight/volume are favorable to the survival of the bacteria in the liquid broth, but not to the same extent as the trehalose treatments.

After 10 weeks, samples were taken from the treatments listed in Table 4 and applied to soya seed. The seeds were incubated at 22° C. Samples were taken initially, after 6 days on the seed, after 2 weeks on the seed, and after 4 weeks on the seed. From these samples, the number of surviving *B japonicum* was assessed. The method of assessing on-seed survival was as described above in Example 1. The results of the on-seed survival are shown in FIG. 6.

Figure 6:
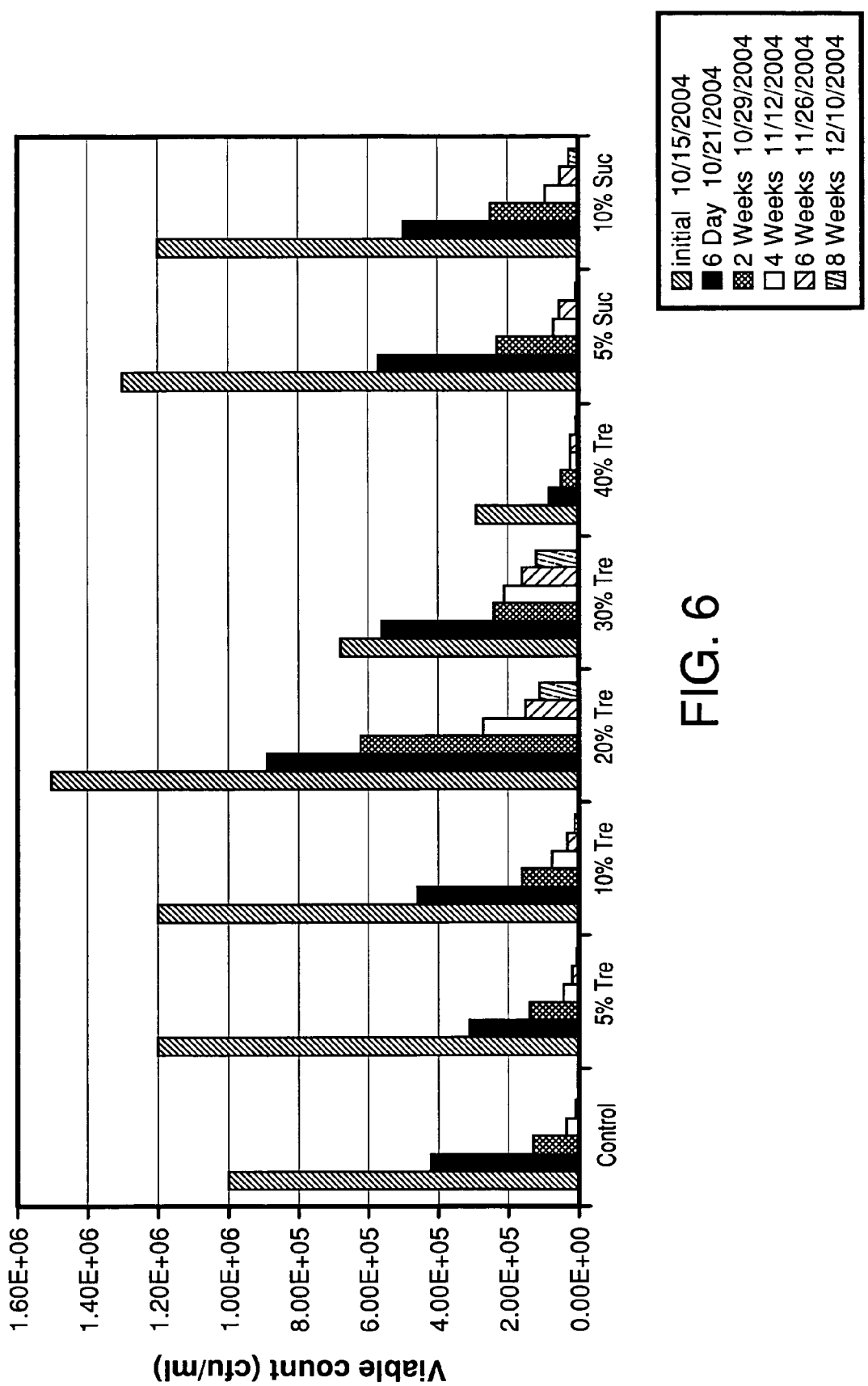
FIG. 6 is a graph of B japonicum survival on seed, as a function of the type and amount of desiccant, resulting from the practice of several embodiments of the present invention.

The results shown in FIG. 6 indicate that at 22° C., treatments with trehalose concentrations between 20% and 30% weight/volume are optimal for survival of the bacteria when the bacteria are placed on seeds.

EXAMPLE 3

Evaluation of Stability of *Serratia Proteomaculans* and *Pseudomonas Fluorescens* in Liquid Broth Formulation

*Serratia proteomaculans* ("*S proteomaculans*") was cultured in a standard microbiological medium (half strength Tryptic soya broth—"TSB") for 24 hours at 22° C. to create a bacterial broth. A set of flasks was prepared, with each flask in the set corresponding to one of the treatments listed in Table 5. 50 ml of the bacterial broth was added to each of the flasks. All the flasks were allowed to equilibrate for an additional 3 days in a shaking incubator at 22° C. The flasks were then transferred to static incubation at 28° C. Periodically samples were taken and bacterial numbers were assessed by preparing serial dilutions and plating onto a half strength Tryptic soya agar—"TSA".

The same steps were repeated for *Pseudomonas fluorescens* ("*P fluorescens*").

TABLE 5

Treatments - Influence of trehalose, sucrose, and glycerol on stability of *S proteomaculans* and *P fluorescens*

| Treatment | Water(g) | Trehalose(g) | Sucrose(g) | Glycerol(g) |
|---|---|---|---|---|
| Control | 50 | 0 | 0 | 0 |
| 10% glycerol | 40 | 0 | 0 | 10 |
| 20% glycerol | 30 | 0 | 0 | 20 |
| 30% glycerol | 20 | 0 | 0 | 30 |
| 10% trehalose | 40 | 10 | 0 | 0 |
| 20% trehalose | 30 | 20 | 0 | 0 |
| 30% trehalose | 20 | 30 | 0 | 0 |
| 10% sucrose | 40 | 0 | 10 | 0 |
| 20% sucrose | 30 | 0 | 20 | 0 |
| 30% sucrose | 20 | 0 | 30 | 0 |

Figure 7:
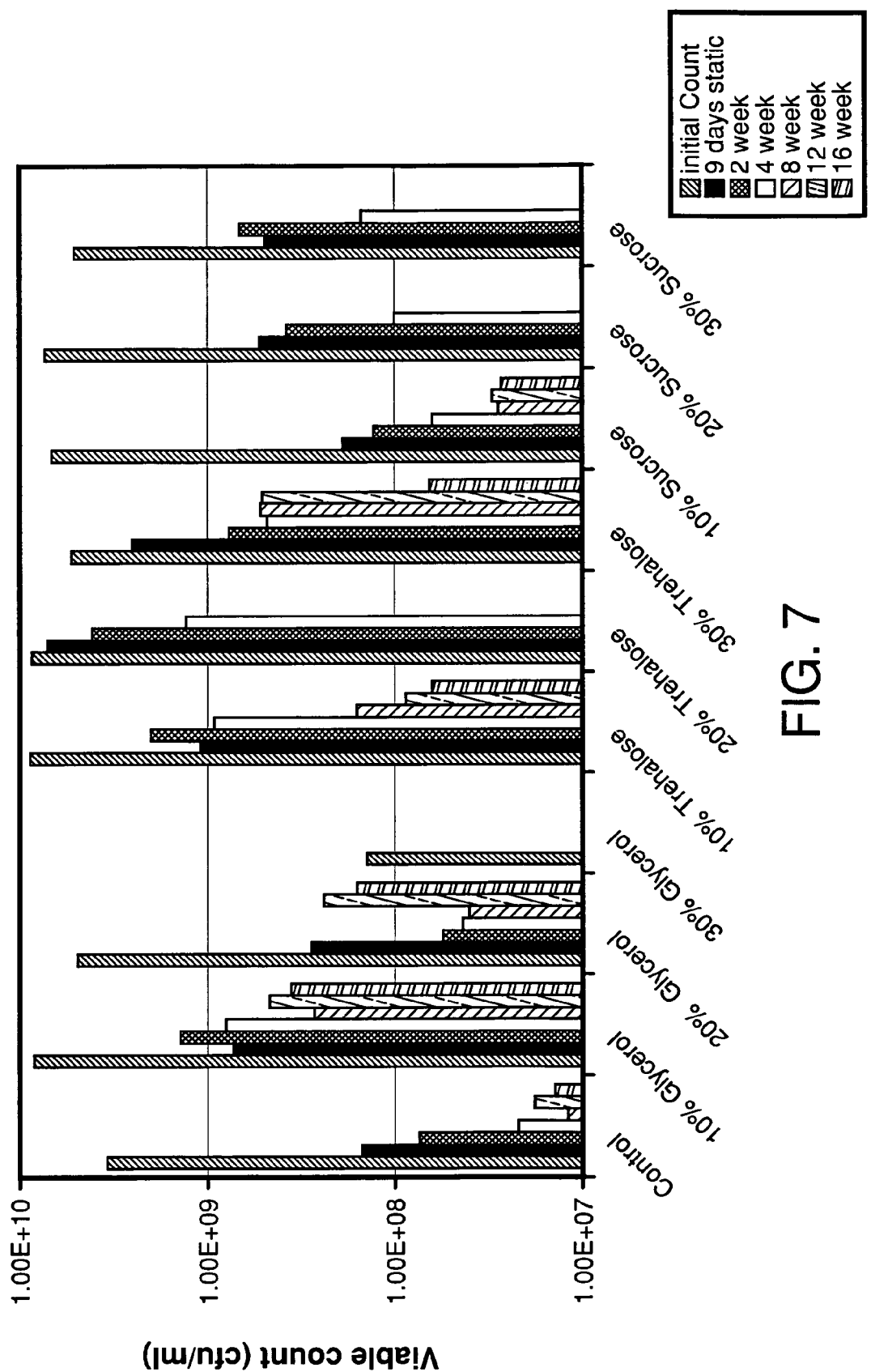
FIG. 7 is a graph of Pseudomonas fluorescens ("P fluorescens") survival in a liquid broth, as a function of the type and amount of desiccant, resulting from the practice of several embodiments of the present invention.

The results of the treatments with regard to the survival of *P fluorescens* in liquid at 28° C. are shown in FIG. 7. The results indicate that at 28° C., treatments with glycerol, trehalose, and sucrose all have the potential to improve survivability of *P fluorescens*.

Figure 8:
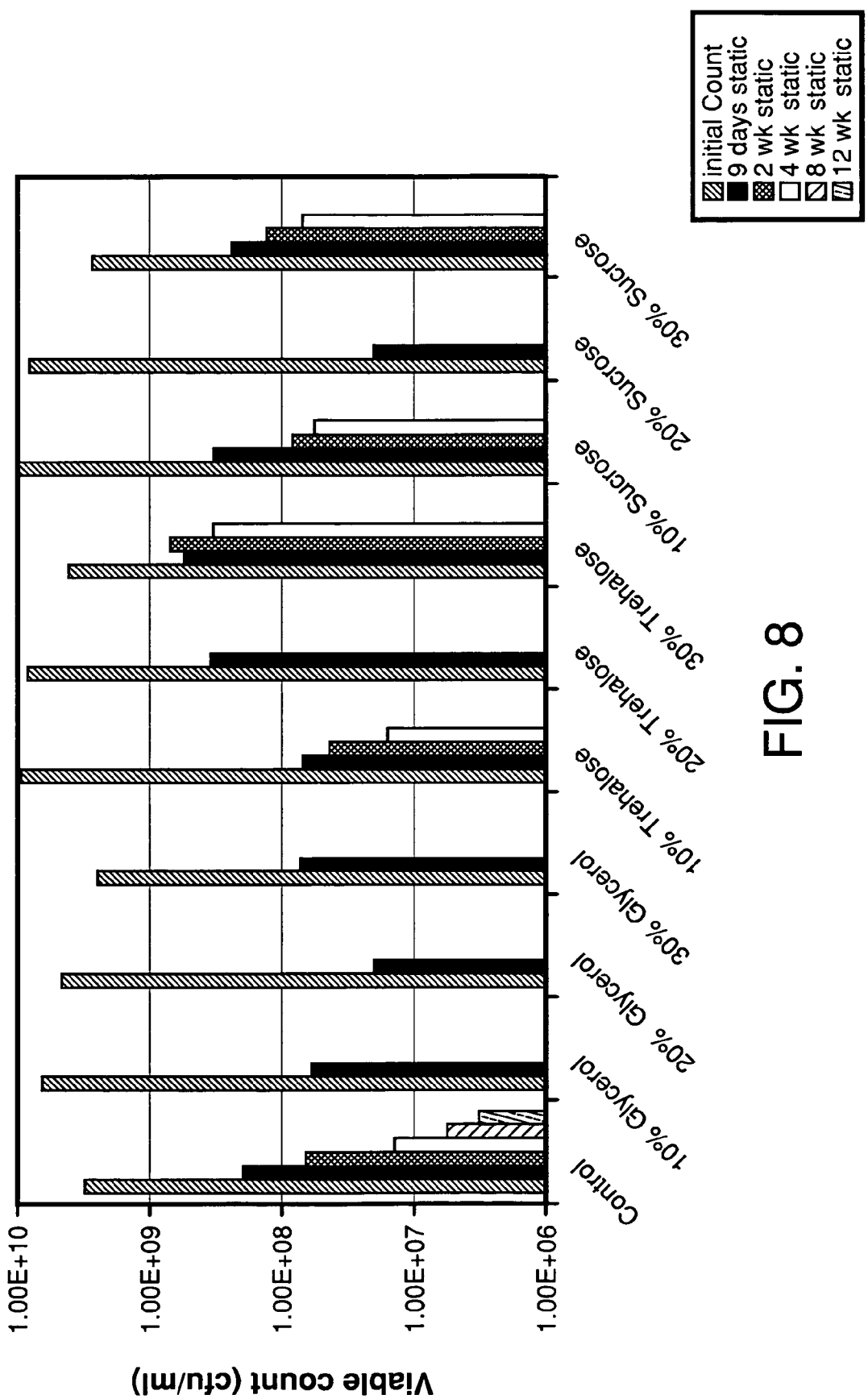
FIG. 8 is a graph of S proteomaculans ("S proteomaculans") survival in a liquid broth, as a function of the type and amount of desiccant, resulting from the practice of several embodiments of the present invention.

The results of the treatments with regard to survival of *S proteomaculans* in liquid at 28° C. are shown in FIG. 8. The results show that for up to 4 weeks, the 30% trehalose treatment, the 10% sucrose treatment, and the 30% sucrose treatment survival counts greater than the control. This data indicates that the treatments have the potential to improve survivability of *S proteomaculans*.

It will be appreciated by those skilled in the art, that the present invention may be practiced in various alternate forms and configurations. The previously detailed description of the disclosed embodiments is presented for purposes of clarity of understanding only, and no unnecessary limitations should be implied there from.

We claim:

1. A method for preparing a partially desiccated liquid inoculant product, the method comprising:
    providing a liquid inoculant comprising bacteria from one or more of the genera *Rhizobium, Bradyrhizobium, Pseudomonas* and *Serratia*, said bacteria grown to a substantially stationary phase; and
    adding to the liquid inoculant, in an amount sufficient to partially desiccate the liquid inoculant, a desiccant treatment comprising a desiccant to form the partially desiccated liquid inoculant product, wherein the desiccant comprises from about 5% to about 50% by weight/volume of the partially desiccated liquid product and wherein the desiccant comprises one or more of trehalose, sucrose or glycerol.

2. The method according to claim 1 wherein water activity of the partially desiccated liquid inoculant product is less than about 0.990.

3. The method according to claim 1 wherein the water activity of the partially desiccated liquid inoculant product is less than about 0.980.

4. The method according to claim 1 wherein the liquid inoculant is provided by:
    introducing bacteria to a liquid nutrient medium to create a bacterial culture; and
    incubating the bacterial culture to allow the bacteria to grow to a substantially stationary phase thereby creating a liquid inoculant.

5. The method according to claim 4 wherein the incubating of the bacterial culture is conducted from about 2 to about 7 days.

6. The method according to claim 1 wherein the desiccant comprises a mixture of two or more of trehalose, sucrose and glycerol.

7. The method according to claim 1 wherein the desiccant is trehalose.

8. The method according to claim 7 wherein the trehalose is from about 10% to about 40% by weight/volume of the partially desiccated liquid inoculant product.

9. The method according to claim 8 wherein the trehalose is from about 20% to about 30% by weight/volume of the partially desiccated liquid inoculant product.

10. The method according to claim 6 wherein the desiccant comprises a mixture of trehalose and glycerol.

11. The method according to claim 10 wherein the trehalose is from about 5% to about 40% by weight/volume of the partially desiccated liquid inoculant product and the glycerol is from about 1% to about 10% by weight/volume of the partially desiccated liquid inoculant product.

12. The method according to claim 11 wherein the trehalose is about 20% by weight/volume of the partially desiccated liquid inoculant product and the glycerol is about 5% by weight/volume of the partially desiccated liquid inoculant product.

13. The method according to claim 1 wherein the method further comprises packaging the partially desiccated liquid inoculant product.

14. The method according to claim 13 wherein the method further comprises storing the partially desiccated liquid inoculant product.

15. The method according to claim 1 wherein the method further comprises applying the partially desiccated liquid inoculant product to a seed.

16. The method according to claim 15 wherein the desiccant is trehalose.

17. The method according to claim 16 wherein the trehalose is from about 10% to about 40% by weight/volume of the partially desiccated liquid inoculant product.

18. The method according to claim 17 wherein the trehalose is from about 20% to about 30% by weight/volume of the partially desiccated liquid inoculant product.

19. The method according to claim 15 wherein the seed comprises a seed for a leguminous plant.

20. The method according to claim 15 wherein the number of bacteria on the seed after about 10 weeks on the seed exceeds about $1 \times 10^5$.

21. The method according to claim 15 wherein the method further comprises applying an extender to the seed after the partially desiccated liquid inoculant product is applied.

22. A method for preparing a dry flowable inoculant formulation, the method comprising:
    providing a liquid inoculant comprising bacteria from one or more of the genera *Rhizobium, Bradyrhizobium, Pseudomonas* and *Serratia*, said bacteria grown to a substantially stationary phase; and adding to the liquid inoculant, in an amount sufficient to partially desiccate the liquid inoculant, a desiccant treatment comprising a desiccant to form the partially desiccated liquid inoculant product; wherein the desiccant comprises from about 5% to about 50% by weight/volume of the partially desiccated liquid product, wherein the desiccant comprises one or more of trehalose, sucrose or glycerol and wherein the partially desiccated liquid inoculant product is applied to a dry carrier to form a dry flowable inoculant formulation.

23. The method according to claim 22 wherein the dry carrier is peat.

24. A method for preparing a partially desiccated liquid inoculant product, the method comprising:

first providing a liquid inoculant comprising bacteria from one or more of the genera *Rhizobium, Bradyrhizobium, Pseudomonas* and *Serratia, said bacteria grown to a substantially stionary phase; and* second adding to the liquid inoculant, in an amount sufficient to partially desiccate the liquid inoculant, a desiccant treatment comprising a desiccant to form the partially desiccated liquid inoculant product, wherein the desiccant comprises from about 5% to about 50% by weight/volume of the partially desiccated liquid product and wherein the desiccant comprises one or more of trehalose, sucrose or glycerol;

third allowing the partially desiccated liquid inoculant product to equilibrate for a predetermined amount of time before applying the partially desiccated liquid inoculant product to seed; and fourth applying the partially desiccated liquid inoculant product to a seed after the predetermined amount of time.

25. The method of claim 24 wherein the predetermined amount of time is about 7 days.

* * * * *